(12) United States Patent
Graff et al.

(10) Patent No.: US 6,380,237 B1
(45) Date of Patent: Apr. 30, 2002

(54) DIPHENYLIMIDAZOLINES

(75) Inventors: Alan Graff; Andrew Plant, both of Leverkusen; Christoph Erdelen, Leichlingen; Norbert Mencke, Leverkusen; Andreas Turberg, Haan, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/743,361

(22) PCT Filed: Jul. 6, 1999

(86) PCT No.: PCT/EP99/04682

§ 371 Date: Feb. 5, 2001

§ 102(e) Date: Feb. 5, 2001

(87) PCT Pub. No.: WO00/03995

PCT Pub. Date: Jan. 27, 2000

(30) Foreign Application Priority Data

Jul. 16, 1998 (DE) .......................... 198 31 987

(51) Int. Cl.$^7$ ..................... A01N 43/50; C07D 233/20; C07D 233/22
(52) U.S. Cl. ................. 514/401; 548/334.1; 548/349.1; 548/348.1; 548/350.1; 548/353.1; 548/347.1; 548/354.1
(58) Field of Search ............................ 548/334.1, 349.1, 548/348.1, 350.1, 353.1, 347.1, 354.1; 514/401

(56) References Cited

U.S. PATENT DOCUMENTS

| | | | |
|---|---|---|---|
| 3,202,674 A | * 8/1965 | Langis et al. ............ 260/309.6 |
| 3,532,464 A | 10/1970 | Friemel ........................ 23/204 |
| 4,255,551 A | 3/1981 | Wolf et al. .................... 528/45 |
| 4,355,058 A | 10/1982 | Gras et al. .................. 427/386 |
| 4,389,371 A | 6/1983 | Wilson et al. ................ 422/15 |
| 4,424,313 A | 1/1984 | Meyer et al. ................ 525/438 |
| 4,452,758 A | 6/1984 | Wilson et al. ................ 422/15 |
| 4,661,600 A | 4/1987 | Goel ........................... 548/217 |
| 4,698,426 A | 10/1987 | Meyer et al. ................ 544/253 |
| 4,242,248 A | 12/1989 | Gras et al. ................ 260/31.2 N |
| 5,283,341 A | 2/1994 | Tanka et al. ............... 548/262.2 |
| 5,466,687 A | 11/1995 | Maier et al. ................ 514/212 |

FOREIGN PATENT DOCUMENTS

| | | |
|---|---|---|
| CA | 2117141 | 9/1994 |
| DE | 25 12 513 | 10/1976 |
| DE | 27 01 372 | 7/1978 |
| DE | 29 46 085 | 5/1981 |
| DE | 32 17 875 | 11/1983 |
| DE | 32 36 598 | 4/1984 |
| DE | 36 10 758 | 10/1987 |
| DE | 40 17 801 | 12/1992 |
| EP | 010852 | * 5/1980 |
| EP | 0 569 326 | 4/1993 |
| FR | 2629092 | 9/1989 |
| GB | 2281072 | 2/1995 |
| WO | 93/04045 | 3/1993 |

OTHER PUBLICATIONS

Molina et al., Synlett, Oct. 1995, pp. 1031–1032.*
Hiyama et al., Tetrahedron, vol. 29, pp. 3137–3139, 1973.*
Chemical Abstract 98:57781 and DD 155296, 1983.
Chemical Abstract 96:147323 & JP 56090982, 1982.
Chemical Abstract 102:36786 & JP 59116660, 1985.
Chemical Abstract 108:167467 & JP 62195369, 1988.
Chemical Abstract 118:23600 & JP 04180944, 1993.
Chemical Abstract 100:213975 & JP 58152085, 1984.
Chrm. Ber 28 (month unavailable) 1895, pp. 3167–3181, Franz Feist und Hugo Artein, Ueber Aromatische Homolog des Aethylendiamins.
Proc. Indian Acad. Sci (Chem. Sci.) vol. 104, No. 3, Jun. 1992, pp. 383–397, K. Nagarajan.
P Rajagopalan, B.G. Advani, V. Ranaga Rao and G.A. Bhat, Synthesis of trans–N–2–aryl(heteryl) Ethenamidines.

* cited by examiner

Primary Examiner—Laura L. Stockton
(74) Attorney, Agent, or Firm—Joseph C. Gil

(57) ABSTRACT

The invention relates to novel diphenylimidazolines of the formula (I)

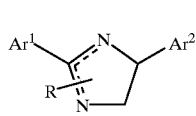

(I)

in which

Ar$^1$, Ar$^2$ and R are each as defined in the description, and a plurality of processes for their preparation and to their use for controlling animal pests.

9 Claims, No Drawings

DIPHENYLIMIDAZOLINES

This application is a 371 of PCT/EP99/04682 filed Jul. 6, 1999.

The invention relates to novel diphenylimidazolines, to processes for their preparation and to their use for controlling animal pests.

Hitherto, only few 2,4-diaryl-4,5-dihydroimidazoles, which are optionally substituted at nitrogen and in the aryl radicals, have been known. The parent compound, 2,4-diphenyl-4,5-dihydro-1H-imidazole was synthesized as early as the 19th century (Chem. Ber. 28, 3172 (1895)). Furthermore, Tetrahedron 29, 3137 (1973) describes the N-methoxycarbamate, SU 466231 (cited in C.A. 83:79277) describes the N-cyclohexyl derivative, EP-A 10 852 describes the N-hydroxyethyl derivative and, finally, Synlett 10, 1031 (1995) describes the 2-para-methyl-4-para-methoxy derivative which is substituted in both phenyl rings and the corresponding mono-substituted compounds. Finally, two compounds which are formally derived from the tautomeric 3H-imidazole are described, 5-(3,4-dimethylphenyl)-1-methyl-2-phenyl-4,5-dihydro-1H-imidazole in Pol. Ann. Univ. Mariae Curie-Skiodowska, Sect. D 36, 111 (1981) and 2-hydroxyphenyl-1-methyl-5-phenyl-4,5-dihydro-1H-imidazole in Proc. Indian Acad. Sci., Chem. Sci. 104, 383 (1992). Without concrete examples, diphenylimidazolines are described in other patent applications: BE 695 703; BE 839 503; BE 846 373; DD 155296 (cited in C.A. 98:57781); DOS 25 12 513; DOS 27 38 270; DOS 29 46 085; DOS 32 04 333; DOS 32 11 301; DOS 32 36 598; DOS 36 10 758; DOS 40 17 801; DOS 42 35 590; EP-A 1 468; EP-A1 516 982; EP-A2 617 069; FR-A1 2629092; JP-A 56 90982 (cited in C.A. 96:147323); JP-A 56 90983 (cited in C.A. 96:147322); JP-A 58 152085 (cited in C.A. 100:213975); JP-A 59 116660 (cited in C.A. 102:36786); JP-A2 62 195369 (cited in C.A. 108:167467) JP-A 04 180944 (cited in C.A. 118:23600); U.S. Pat. No. 3,202,674; U.S. Pat. No. 4,066,625; U.S. Pat. No. 4,661,600; WO 93/04045; WO 93/04046; derivatives which are substituted in both phenyl rings are described in DOS 27 01 372 (only methyl or ethyl substituents), DOS 32 17 875 (if the $C_6$–$C_{15}$-aryl radical is understood as, for example, tolyl or xylyl), in U.S. Pat. No. 4,389,371 and U.S. Pat. No. 4,452,758 (exclusively alkali metal salts of N-(alkoxy)-alkyl-carboxylic acids) and DOS 27 44 782 and EP-A1 596 326 (specific heterocyclylmethyl substituent).

Hitherto, nothing has been known concerning the use of 2,4-diaryl-4,5-dihydroimidazoles as pesticides.

This invention, accordingly, provides novel diarylimidazolines of the formula (I)

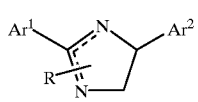

in which
Ar¹ represents the grouping (a)

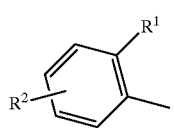

in which
$R^1$ represents halogen, alkyl, alkoxy or halogenoalkoxy and
$R^2$ represents hydrogen, halogen, alkyl or alkoxy, Ar² represents the grouping (b) or (c)

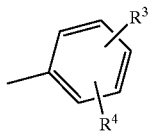

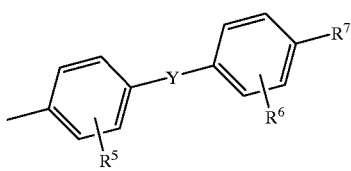

in which
$R^3$, $R^4$, $R^5$ and $R^6$ independently of one another each represent hydrogen, halogen, alkyl, alkoxy, halogenoalkoxy or halogenoalkylthio,
$R^7$ represents hydrogen, halogen, cyano, alkyl, alkoxy, alkylthio, halogenoalkyl, halogenoalkoxy or halogenoalkylthio and
Y represents a direct bond, oxygen, methylene, —O—CH₂— or —CH₂O— and
R represents cyano, alkoxyalkyl, formyl, alkylcarbonyl, alkoxycarbonyl or —C(X)—NHR⁸ in which
X represents oxygen or sulphur and
$R^8$ represents hydrogen or alkyl.
Here, halogen represents F, Cl, Br and iodine, in particular F, Cl and Br.

The compounds of the formula (I) include N-substituted derivatives of the two tautomeric forms of the cyclic imidate function which forms the basis for the imidazoline. These compounds are 1H-4,5-dihydroimidazoles of the formula (I)$_a$ and 3H-4,5-dihydroimidazoles of the formula (I)$_b$ which is intended to be expressed by the dotted line in the formula (I).

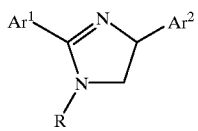

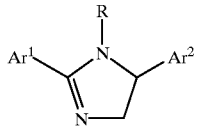

The compounds of the formulae (I)$_a$ and (I)$_b$ can be present both as mixtures or in the form of the pure isomers and furthermore, depending, inter alia, on the kind of substituents, as geometric and/or optical isomers or isomer mixtures of varying composition. These isomers can, if appropriate, be separated in a customary manner. The invention relates both to the pure isomers and to their mixtures.

Furthermore, it has been found that the novel compounds of the formula (I) are obtained by one of the processes described below.

A) Diphenylimidazolines of the formula (I-a)

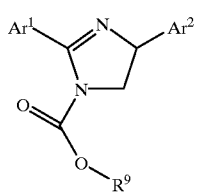

(I-a)

in which
Ar$^1$ and Ar$^2$ are each as defined above and
R$^9$ represents C$_1$–C$_4$-alkyl,
are obtained by condensing β-chlorocarbamates of the formula (II)

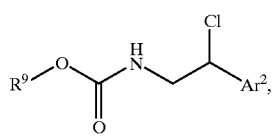

(II)

in which
Ar$^2$ and R$^9$ are each as defined above
with benzonitriles of the formula (III)

Ar$^1$—CN  (III), in which
Ar$^1$ is as defined above in the presence of sulphuric acid, or B) diphenylimidazolines of the formula (I-b)

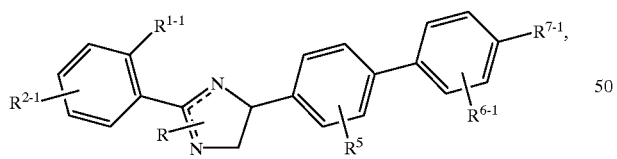

(I-b)

in which
R is as defined above and
R$^{1-1}$ represents fluorine, chlorine, alkyl, alkoxy or halogenoalkoxy,
R$^{2-1}$ represents hydrogen, fluorine, chlorine, alkyl or alkoxy,
R$^{5-1}$ and R$^{6-1}$ independently of one another each represent hydrogen, fluorine, chlorine, alkyl, alkoxy, halogenoalkyl or halogenoalkylthio and
R$^{7-1}$ represents hydrogen, fluorine, chlorine, cyano, alkyl, alkoxy, alkylthio, halogenoalkyl or halogenoalkylthio are obtained by coupling halogen compounds of the formula (I-c)

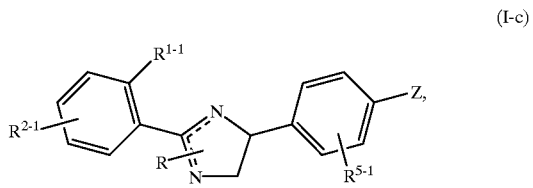

(I-c)

in which
R, R$^{1-1}$, R$^{2-1}$ and R$^{5-1}$ are each as defined above and
Z represents bromine or iodine
with boronic acids of the formula (IV)

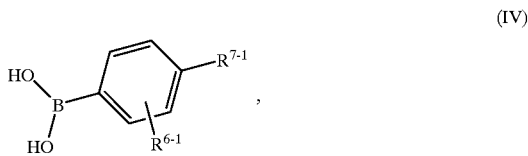

(IV)

in which
R$^{6-1}$ and R$^{7-1}$ are each as defined above
in the presence of a catalyst and, if appropriate, in the presence of an acid binder and, if appropriate, in the presence of a diluent, or C) diphenylimidazolines of the formula (I)

(I)

in which
Ar$^1$, Ar$^2$ and R are each as defined above
are obtained by condensing diphenylimidazolines of the formula (V)

(V)

which are not substituted at nitrogen and in which
Ar$^1$ and Ar$^2$ are each as defined above
with compounds of the formula (VI)

R—X$^1$  (VI), in which
R is as defined above and
X$^1$ represents, depending on the radical R, a suitable leaving group, such as —Cl, —Br, —OSO$_2$OR$^{10}$ or —OR$^{10}$
in which
R$^{10}$ represents alkyl or aryl,
if appropriate in the presence of a reaction auxiliary, or D) diphenylimidazolines of the formula (I-d)

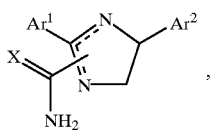
(I-d)

in which
Ar¹, Ar² and X are each as defined above
are obtained by reacting nitrites of the formula (I-e)

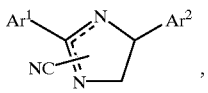
(I-e)

in which
Ar¹ and Ar² are each as defined above
with water or hydrogen sulphide, if appropriate in the presence of a reaction auxiliary.

Furthermore, it has been found that the compounds of the formula (I) and their biologically active salts are suitable for controlling animal pests, in particular insects, arachnids and nematodes.

The formula (I) provides a general definition of the novel compounds. Preferred substituents or ranges of the radicals listed in the formulae mentioned hereinabove and hereinbelow are illustrated below.

Ar¹ particularly represents the grouping (a)

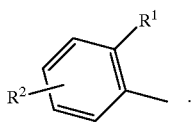
(a)

Ar² particularly represents the grouping (b) or (c)

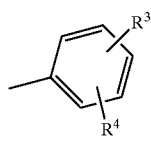
(b)

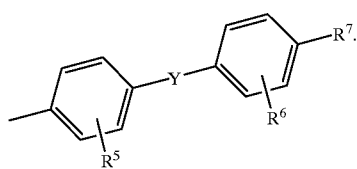
(c)

R particularly represents cyano, $C_1$–$C_4$-alkoxy-$C_1$–$C_4$-alkyl, $C_1$–$C_4$-alkylcarbonyl, $C_1$–$C_4$-alkoxycarbonyl or —C(X)—NHR⁸.

R¹ particularly represents halogen, $C_1$–$C_3$-alkyl, $C_1$–$C_3$-alkoxy or $C_1$–$C_3$-halogenoalkoxy.

R² particularly represents hydrogen, halogen, $C_1$–$C_3$-alkyl or $C_1$–$C_3$-alkoxy.

R³, R⁴, R⁵ and R⁶ independently of one another each particularly represent hydrogen, halogen, $C_1$–$C_{12}$-alkyl or $C_1$–$C_{12}$-alkoxy.

R⁷ particularly represents hydrogen, halogen, cyano, $C_1$–$C_6$-alkyl, $C_1$–$C_6$-alkoxy, $C_1$–$C_6$-alkylthio, $C_1$–$C_6$-halogenoalkyl, $C_1$–$C_4$-halogenoalkoxy or $C_1$–$C_4$-halogenoalkylthio.

R⁸ particularly represents hydrogen or $C_1$–$C_4$-alkyl.

X particularly represents oxygen or sulphur.

Y particularly represents a direct bond or oxygen.

Here, halogen preferably represents F, Cl, Br and iodine, in particular F, Cl and Br.

Ar¹ particularly preferably represents the grouping (a)

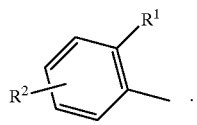
(a)

Ar² particularly preferably represents the grouping (b-a) or (c-a)

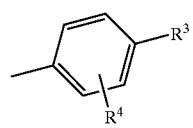
(b-a)

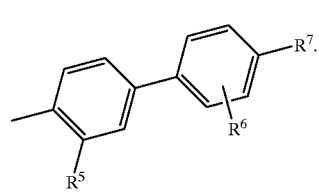
(c-a)

R particularly preferably represents cyano, $C_1$–$C_3$-alkoxy-$C_1$–$C_3$-alkyl, $C_1$–$C_3$-alkylcarbonyl, $C_1$–$C_2$-alkoxycarbonyl or —C(X)—NHR⁸.

R¹ particularly preferably represents fluorine, chlorine, bromine, iodine, $C_1$–$C_3$-alkyl and $C_1$–$C_3$-alkoxy.

R² particularly preferably represents hydrogen, fluorine, chlorine, bromine, $C_1$–$C_3$-alkyl or $C_1$–$C_3$-alkoxy.

R³, R⁴, R⁵ and R⁶ independently of one another each particularly preferably represent hydrogen, fluorine, chlorine, bromine, iodine, $C_1$–$C_6$-alkyl or $C_1$–$C_6$-alkoxy.

R⁷ particularly preferably represents hydrogen, fluorine, chlorine, bromine, iodine, cyano, $C_1$–$C_4$-alkyl, $C_1$–$C_4$-alkoxy, $C_1$–$C_4$-alkylthio, fluorine- or chlorine-substituted $C_1$–$C_4$-alkyl, $C_1$–$C_4$-alkoxy or $C_1$–$C_4$-alkylthio.

R⁸ particularly preferably represents hydrogen or $C_1$–$C_4$-alkyl.

X particularly preferably represents oxygen or sulphur.

Ar¹ very particularly preferably represents the grouping (a-1), (a-2) or (a-3)

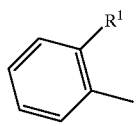
(a-1)

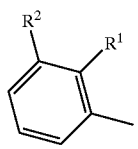
(a-2)

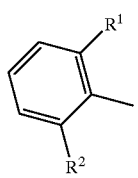
(a-3)

Ar² very particularly preferably represents the grouping (b-b) or (c-b)

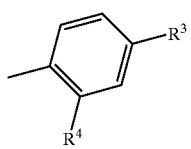
(b-b)

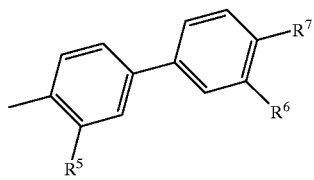
(c-b)

R very particularly preferably represents cyano, ethoxymethyl, acetyl, propionyl, butyryl, methoxycarbonyl, ethoxycarbonyl or —C(X)—NHR⁸.

R¹ very particularly preferably represents fluorine, chlorine, bromine, methyl, ethyl, methoxy or ethoxy.

R² very particularly preferably represents hydrogen, fluorine, chlorine, bromine, methyl, ethyl, methoxy or ethoxy.

R³, R⁴, R⁵ and R⁶ independently of one another each very particularly preferably represent hydrogen, fluorine, chlorine, bromine, methyl, ethyl, n-propyl, isopropyl, n-butyl, isobutyl, sec-butyl, tert-butyl, pentyl, hexyl, methoxy, ethoxy, n-propoxy, isopropoxy, n-butoxy, isobutoxy, sec-butoxy, tert-butoxy, pentyloxy or hexyloxy.

R⁷ very particularly preferably represents fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, methylthio, ethylthio, n-propylthio, isopropylthio, difluoromethyl, trifluoromethyl, dichloromethyl, trichloromethyl, difluoromethoxy, trifluoromethoxy, chlorodifluoromethoxy, 1,1-difluoroethoxy, 1,1,2-trifluoroethoxy, 1,1,2,2-tetrafluoroethoxy, 2-chloro-1,1,2-trifluoroethoxy, 2,2,2-trichloro-1,1-difluoroethoxy, pentafluoroethoxy, difluoromethylthio, trifluoromethylthio, chlorodifluoromethylthio, 1,1-difluoroethylthio, 1,1,2-trifluoroethylthio, 2,2,2-trifluoroethylthio, 1,1,2,2-tetrafluoroethylthio, 2-chloro-1,1,2-trifluoroethylthio, 2,2,2-trichloro-1,1-difluoroethylthio or pentafluoroethylthio.

R⁸ very particularly preferably represents hydrogen, methyl or ethyl.

X very particularly preferably represents oxygen of sulphur.

Ar¹ in particular very particularly preferably represents the grouping (a-3)

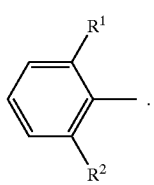
(a-3)

Ar² in particular very particularly preferably represents the grouping (b-c)

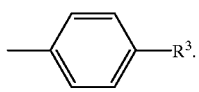
(b-c)

R¹ and R² are identical or different and in particular very particularly preferably represent hydrogen, F, Cl, CH₃ or ethyl, where R¹ and R² are not simultaneously hydrogen.

R³ in particular very particularly preferably represents bromine, substituted phenyl or phenoxy, suitable substituents being —OCF₃, —SCF₃ or t-butyl.

R in particular very particularly preferably represents methyl, ethyl, propyl, i-propyl, cyano,

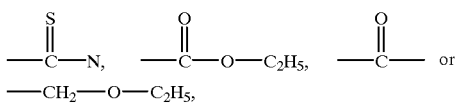
—CH₂—O—C₂H₅,

Ar¹ very especially particularly preferably represents the grouping (a-3)

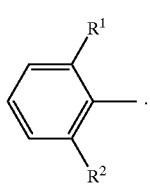
(a-3)

Ar² very especially particularly preferably represents the grouping (b-c)

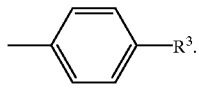
(b-c)

R¹ and R² are identical or different and very especially particularly preferably represent F, Cl and hydrogen, where R¹ and R² do not simultaneously represent hydrogen.

R³ very especially particularly preferably represents bromine or 4-trifluoromethoxyphenyl.

R very especially particularly preferably represents

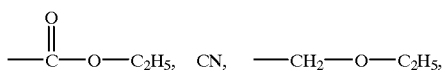

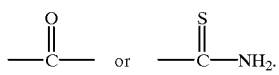

The abovementioned general or preferred radical definitions or illustrations can be combined with each other at will, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

In particular very particularly preferred according to the invention are the compounds of the formula (I) which contain a combination of the meanings listed above as being in particular very particularly preferred.

Very especially particularly preferred according to the invention are the compounds of the formula (I) which contain a combination of the meanings listed above as being very especially particularly preferred.

Saturated or unsaturated hydrocarbon radicals such as alkyl can in each case be straight-chain or branched, including in combination with heteroatoms, such as, for example, in alkoxy.

Optionally substituted radicals may be mono- or polysubstituted, and in the case of polysubstitution, the substituents may be identical or different.

Using, for example, ethyl N-[2-chloroethyl-2-(3-methylphenyl)]-carbamate and 2-propylbenzonitrile as starting materials, the course of the reaction of the process (A) according to the invention can be represented by the following equation:

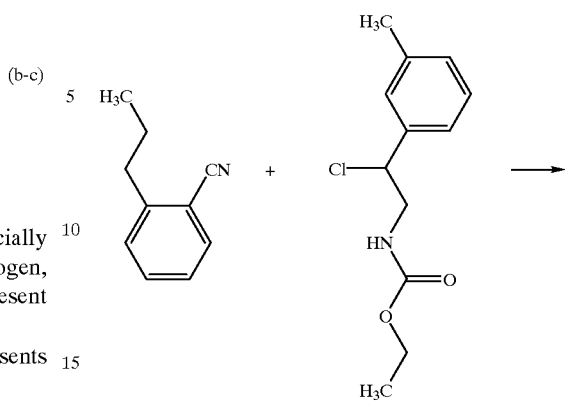

Using, for example, 4-(4-bromophenyl)-1-ethoxycarbonyl-2-(2,6-difluorophenyl)-4,5-dihydro-1H-imidazole and 4-methylphenylboronic acid as starting materials, the course of the reaction in the process (B) according to the invention can be represented by the following equation:

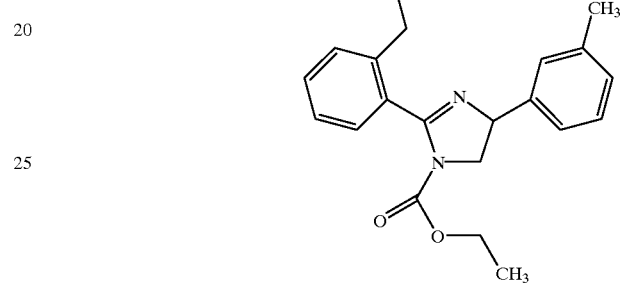

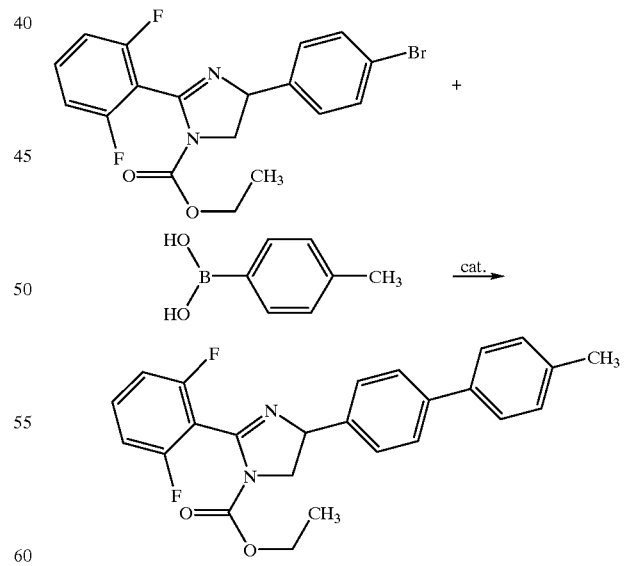

Using, for example, 4-(2-chlorophenyl)-2-(2,6-difluorophenyl)-4,5-dihydro-1H-imidazole and N-methylcarbamoyl chloride as starting materials, the course of the reaction of the process (C) according to the invention can be represented by the following equation:

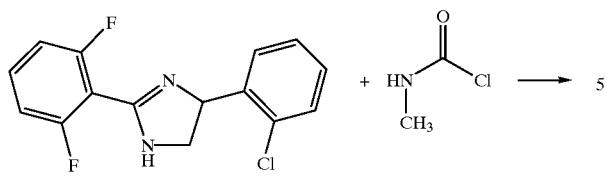

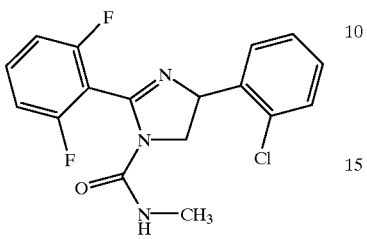

Reacting, for example, 4-(2-chlorophenyl)-1-cyano-2-(2,6-difluorophenyl)-4,5-dihydro-1H-imidazole as starting material with aqueous sulphuric acid, the course of the reaction of the process (D) according to the invention can be represented by the following equation:

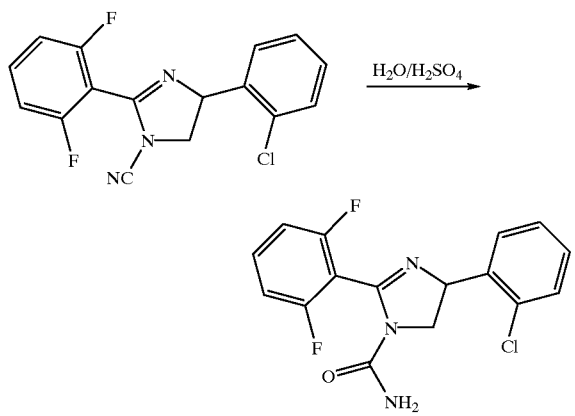

The formula (II) provides a general definition of the β-chlorocarbamates required for carrying out the process (A) according to the invention. In this formula, $Ar^2$ and $R^9$ preferably have those meanings which have already been mentioned as being preferred in connection with the description of the diarylimidazolines of the formula (I).

β-chlorocarbamates of the formula (II) can be prepared, for example, by adding ethyl N,N-dichlorocarbamates of the formula (VII) to styrenes of the formula (VIII) in a dipolar-aprotic solvent such as, for example, acetonitrile, at temperatures between −20 and +20° C., and dehalogenating the N-chlorocarbamide which is initially formed with a reducing agent such as, for example, bisulphite solution, according to the equation below:

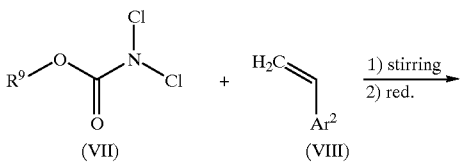

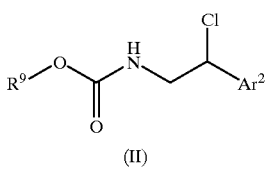

Some of the ethyl N,N-dichlorocarbamates of the formula (VII) are commercially available, known from the literature or obtainable by known processes (see, for example, Thomas A. Foglia, Daniel Swern, J. Org. Chem. 31 (1966) 3625–3631; Ronald E. White, Peter Kovacic, J. Am. Chem. Soc. 97 (1975) 1180–1184).

The formula (III) provides a general definition of the benzonitriles furthermore required for carrying out the process (A) according to the invention. In this formula, $Ar^1$ preferably has that meaning which has already been mentioned in connection with the description of the diarylimidazolines of the formula (I) as being preferred.

The benzonitriles of the formula (III) and the styrenes of the formula (VIII) are generally known compounds of organic chemistry (see textbooks of organic chemistry, such as, for example, Beyer-Walter, Lehrbuch der organischen Chernie, 21st edition, 1988), and some of them are commercially available.

The halogen compounds of the formula (I-c) required for carrying out the process (B) according to the invention are a subset of the compounds of the general formula (I) according to the invention and can be prepared, for example, according to processes (A), (C) or (D).

The formula (IV) provides a general definition of the boronic acids furthermore required for carrying out the process (B) according to the invention. In this formula, $R^{6-1}$ and $R^{7-1}$ preferably have those meanings which have already been mentioned in connection with the description of the diarylimidazolines of the formula (I) as being preferred, except for bromine and iodine.

Some of the aromatic boronic acids of the formula (IV) are commercially available, and are known from the literature, or they can be prepared similarly to known methods [cf. Chem. Rev. 45, 2457 (1995); Pure Appl. Chem. 66, 213 (1994)].

The formula (V) provides a general definition of the diarylimidazolines required for carrying out the process (C) according to the invention. In this formula, $Ar^1$ and $Ar^2$ preferably have those meanings which have already been mentioned in connection with the description of the N-substituted diarylimidazolines of the formula (I) as being preferred. The diarylimidazolines of the formula (V) are novel and likewise form part of the subject-matter of the present application.

Diarylimidazolines of the formula (V) can be prepared, for example, by cleaving carbamates of the formula (I-a) with alkali metal hydroxides such as, for example, potassium hydroxide in the presence of a solubilizer such as, for example, ethanol at temperatures of from 20 to 120° C., according to the following equation:

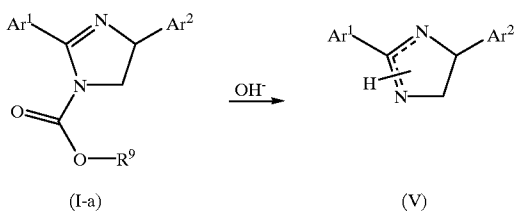

(I-a)        (V)

The carbamates of the formula (I-a) are a subset of the compounds of the general formula (I) according to the invention and can be prepared, for example, according to process (A).

The N-cyanodiphenylimidazolines of the formula (I-d) required for carrying out the process (D) according to the invention are a subset of the compounds of the general formula (I) according to the invention and can be prepared, for example, according to process (C).

The process (A) according to the invention is carried out in the presence of (aqueous) sulphuric acid. In general, the process is carried out at concentrations of from 80 to 100%.

In the case of the process (A) according to the invention, the reaction temperature can be varied within a relatively wide range. In general, the reaction is carried out at temperatures between −20° C. and +50° C., preferably between 0 and 30° C.

When carrying out the process (A) according to the invention, generally 0.5 to 3 mol, preferably 1 to 2 mol, of benzonitrile of the formula (III) is employed per mole of β-chlorocarbamate of the formula (II). Here, the acid is employed in a large, for example 2- to 20-fold, excess, and, if appropriate, the reaction is carried out using the acid as solvent.

For carrying out the process (B) according to the invention, palladium complexes are suitable for use as catalysts. Preferred catalysts are, for example, tetrakis(triphenylphosphine)palladium and dichloro-bis(triphenylphosphine)palladium.

Suitable acid acceptors for carrying out the process (B) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (B) according to the invention are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro- trichloroethane or tetrachloroethylene; ethers, such as, for example, diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as, for example, methanol, ethanol, n- or iso-propanol, n-, iso-, sec- or tert-butanol, ethanediol, propane-1,2-diol, ethoxyethanol, methoxyethanol, diethylene glycol monomethyl ether, diethylene glycol monoethyl ether; water.

In the case of the process (B) according to the invention, the reaction temperature can be varied within a relatively wide range. In general, the reaction is carried out at temperatures between 0° C. and +140° C., preferably between 50° C. and +100° C.

When carrying out the process (B) according to the invention, the boronic acid of the formula (IV) and the halogen compound of the formula (I-c) are employed in a molar ratio of from 1:1 to 3:1, preferably from 1:1 to 2:1. In general, 0.005 to 0.5 mol, preferably 0.01 mol to 0.1 mol, of catalyst are employed per mole of the compound of the formula (I-c). In general, an excess of base is employed.

The process (C) according to the invention is carried out in the presence of a suitable reaction auxiliary. Suitable reaction auxiliaries are all customary inorganic or organic bases. These preferably include alkaline earth metals or alkali metal hydrides, hydroxides, amides, alkoxides, acetates, carbonates or bicarbonates, such as, for example, sodium hydride, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

If appropriate, the process (C) according to the invention can be carried out in the presence of a suitable phase-transfer catalyst. Examples of such catalysts include: tetrabutylammonium iodide, tetrabutylammonium bromide or tetrabutylammonium chloride, tributylmethylphosphonium bromide, trimethyl-$C_{13}$/$C_{15}$-alkylammonium chloride or trimethyl-$C_{13}$/$C_{15}$-alkylammonium bromide, dibenzyldimethylammonium methylsulphate, dimethyl-$C_{12}$/$C_{14}$-alkylbenzylammonium chloride, 15-crown-5, 18-crown-6 or tris[2-(2-methoxyethoxy)-ethyl]-amine.

The process (C) according to the invention is preferably carried out in the presence of a diluent. Suitable diluents are water, organic solvents and any mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as, for example, diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; ketones, such as, for example, acetone, butanone, methyl isobutyl ketone or cyclohexanone; nitriles, such as, for example, acetonitrile, propionitrile, n- or iso-butyronitrile or benzonitrile; amides, such as, for example, formamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as, for example, methyl acetate, ethyl acetate or butyl acetate; sulphoxides, such as, for example, dimethyl sulphoxide; sulphones, such as sulpholane; alcohols, such as, for example, methanol, ethanol, n- or iso-propanol, n-, iso-, sec- or tert-butanol, ethanediol, propane-1,2-diol, ethoxyethanol, methoxyethanol, diethylene glycol monomethyl ether, diethylene glycol monoethyl ether; water.

In the case of the process (C) according to the invention, the reaction temperature can be varied within a relatively wide range. In general, the reaction is carried out at temperatures between −20° C. and +100° C., preferably between 0° C. and 60° C.

When carrying out the process (C) according to the invention, in general from 1 to 5 mol of the compound of the formula (VI) are employed per mole of the compound of the formula (V). However, whenever it is expedient, for example in the case of a gaseous reagent, it is possible to employ a larger excess of the compound of the formula (VI).

The process (D) according to the invention is carried out in the presence of a reaction auxiliary. When reacting with hydrogen sulphide, use is made, for example, of tertiary amines, such as pyridine or triethylamine. These may simultaneously serve as diluents. In the reaction with water, use is made, for example, of aqueous mineral acids, such as sulphuric acid or hydrochloric acid, preferably 96% strength sulphuric acid. The acids may likewise simultaneously serve as diluent.

In the case of the process (D) according to the invention, the reaction temperature can be varied within a relatively wide range. In general, the reaction is carried out at temperatures between −20° C. and +100° C., preferably between 0° C. and 60° C.

The amount of hydrogen sulphide or water employed when carrying out the process (D) according to the invention is not critical. At least 1 mol of hydrogen sulphide or water is required per mole of nitrile of the formula (I-e). In the case of hydrogen sulphide, it is advantageous to employ a larger excess.

The reactions of the processes (A to D) according to the invention can be carried out at atmospheric pressure or under elevated pressure. Preference is given to carrying out the processes at atmospheric pressure. The practice of the reactions, the work-up and the isolation of the reaction products is carried out according to customary, known methods. The end products are preferably purified by crystallization, chromatographic separation or by removing the volatile components, if appropriate under reduced pressure (cf. also the preparation examples).

The active compounds, having good crop tolerance and favourable homeotherm safety, are suitable for controlling animal pests, in particular insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus human corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp, *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidius, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyarni, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The plant-parasitic nematodes include, for example, Pratylenchus spp., *Radopholus similis, Ditylenchus dipsaci, Tylenchulus sernipenetrans*, Heterodera spp., Meloidogyne spp., Aphelenchoides spp., Longidorus spp., Xiphinema spp. and Trichodorus spp.

The active compounds of the formula (I) according to the invention have, in particular, excellent activity against the larvae of the mustard beetle (*Phaedon cochleariae*), against the caterpillars of the owlet moth (*Spodoptera frugiperda*) and against all stages of the greenhouse red spider mite (*Tetranychus urticae*).

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents, for example, can also be used as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; dispersing agents suitable are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas, substances produced by microorganisms, etc.

Examples of particularly advantageous mixture components are the following compounds:
Fungicides:
2-aminobutane; 2-anilino4-methyl-6-cyclopropylpyrimidine; 2',6'-dibromo-2-methyl-4'-trifluoromethoxy-4'-trifluoro-methyl-1,3-thiazole-5-carboxamide; 2,6-dichloro-N-(4-trifluoromethylbenzyl)-benzamide; (E)-2-methoxyirnino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metirarn, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procyrnidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:

abamectin, acephate, acetarniprid, acrinathrin, alanycarb, aldicarb, aldoxycarb, alpha-cypermethrin, alphamethrin, arnitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, terivinphos, terbufos, tetrachlorvinphos, thetacypernethrin, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, varmidothion, vaniliprole, Verticillium lecanii,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N- [[[4-(2,2-dichloro-1,1-difluoroethoxy)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

A mixture with other known active compounds such as herbicides, or with fertilizers and growth regulators is also possible.

The active compound according to the invention can furthermore be present in its commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound is distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola From the order Diptera and the sub-orders Nematocerina and Brachycerina, for example, Aedes spp., Anopheles spp., Culex spp., Simulium spp., Eusimulium spp., Phiebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica*, Supella spp.

From the subclass of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneu-monyssus spp., Sternostoma spp., Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

The active compounds of the formula (I) according to the invention show, for example, excellent activity against all larval stages of the fly *Lucillia cuprina*.

The active compounds according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey etc.), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices, etc.

When administered to livestock, poultry, domestic animals etc., the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as
*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Zyleborus spec., Tryptodendron spec., *Apate monachus, Bostrychus capucins, Heterobostrychus brunneus,* Sinoxylon spec., *Dinoderus minutus.*

Dermapterans, such as
*Sirex juvencus, Urocerus gigas, Urocerus gigas taignus, Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-living materials such as, preferably, synthetic materials, glues, sizes, paper and board, leather, wood and timber products, and paint.

The materials to be protected very particularly against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colourants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture likewise has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colourants, pigments, water repellents, odour-masking substances and inhibitors or anticorrosives known per se and the like can be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of phthalic esters, such as dibutyl phthalate, dioctyl phthalate or benzylbutyl phthalate, phosphoric esters, such as tributyl phosphate, adipic esters, such as di-(2-ethylhexyl) adipate, stearates, such as butyl stearate or amyl stearate, oleates, such as butyl oleate, glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanid, tolylfluanid, 3-iodo-2-propinylbutyl carbamate, N-octyl-isothiazolin-3-one and 4,5-dichloro-N-octylisothiazolin-3-one.

The preparation and the use of the active compounds according to the invention can be seen from the examples below.

PREPARATION EXAMPLES

Example I-1

(Process A)

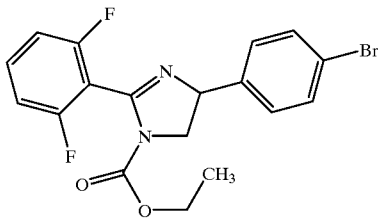

3.1 g (10 mmol) of ethyl N-[2-(4-bromophenyl)-2-chloroethyl]-carbamate (for example from Example II-1) and 2.09 g (15 mmol) of 2,6-difluorobenzonitrile were dissolved in 10 ml of conc. sulphuric acid and stirred at room temperature for three hours, during which the colour of the solution turned dark. After this, the mixture was carefully poured onto ice. It was extracted 2x with dichloromethane and the aqueous phase was made alkaline with sodium hydroxide and once more extracted. The combined organic phases were extracted with saturated sodium chloride solution, dried and concentrated. The 4.4 g of crude product which had been obtained were chromatographed over a silica gel column (cyclohexane: ethyl acetate=5:1). This gave 3.6 g (88% of theory) of 4-(4-bromophenyl)-1-ethoxycarbonyl-2-(2,6-difluorophenyl)-4,5-dihydro-1H-imidazol as a viscous yellow oil.

¹H NMR (400 MHz, CDCl₃): δ [ppm] 1.1 (t, 3H); 3.7 (m, 1H); 4.1 (q, 2H); 4.4 (m, 1H); 5.4 (m, 1H); 6.9–7.6 (m, 7H).

Example I-2

(Process A)

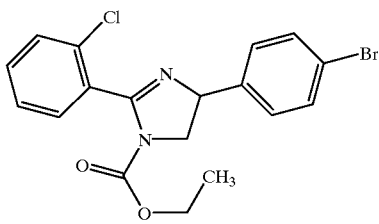

By the method of Example I-1, 3.1 g (10 mmol) of ethyl N-[2-(4-bromophenyl)-2-chloroethyl]-carbamate (for example from Example II-1) and 2.1 g of (15 mmol) 2-chlorobenzonitrile gave 2.9 g (72% of theory) of 4-(4-bromophenyl)-2-(2-chlorophenyl)-1-ethoxycarbonyl-4,5-dihydro-1H-imidazole as a viscous colourless oil.

¹H NMR (400 MHz, CDCl₃): δ [ppm] 1.0 (t, 3H); 3.9 (m, 1H); 4.0 (q, 2H); 4.4 (m, 1H); 5.3 (m, 1H); 7.2–7.6 (m, 8H).

Example I-3

(Process B)

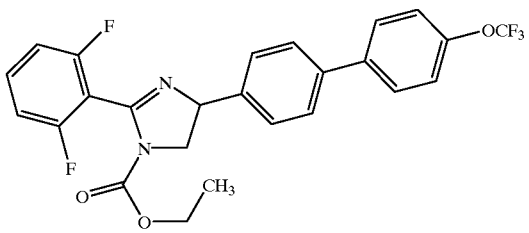

3.6 g (9 mmol) of 4-(4-bromophenyl)-1-ethoxycarbonyl-2-(2,6-difluorophenyl)-4,5-dihydro-1H-imidazole (for example from Example I-1) were dissolved in 25 ml of dimethoxyethane and admixed with 20 ml of a 1M solution of sodium carbonate. 2.9 g (11 mmol) of 4-trifluoromethoxyphenylboronic acid (85% strength) and finally, as catalyst, 336 mg (0.48 mmol) of dichloro-bis (triphenylphosphino)palladium(II) were added to this mixture. The mixture, which was initially yellow, was heated at reflux, giving a brown solution. The mixture was boiled overnight and, after cooling, admixed with water and extracted with ethyl acetate. The combined extracts were washed successively with ammonium chloride solution, water and sodium chloride solution, concentrated and chromatographed over a silica gel column (cyclohexane:ethyl acetate=10:1). This gave 2.50 g (57% of theory) of 1-ethoxycarbonyl4-(4'-trifluoromethoxy-4-biphenylyl)-2-(2,6-difluoro-phenyl)-4,5-dihydro-1H-imidazole.

M.p.: 105–107° C.

Example I-4

(Process B)

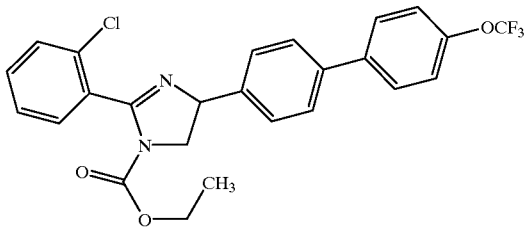

By the method of Example I-3, 1.5 g (9.0 mmol) of 4-(4-bromophenyl)-2-(2-chloro-phenyl)-1-ethoxycarbonyl4,5-dihydro-1H-imidazole (for example from Example I-2) and 1.0 g (4.8 mmol) of 4-trifluoromethoxyphenylboronic acid gave 1.38 g (76% of theory) of 2-(2-chlorophenyl)-1-ethoxycarbonyl-4-(4'-trifluormethoxy-4-biphenylyl)-4,5-dihydro-1H-imidazole as a colourless oil.

$^1$H NMR (400 MHz, CDCl$_3$): δ [ppm] 1.0 (t, 3H); 3.9 (m, 1H); 4.0 (q, 2H); 4.4 (m, 1H); 5.4 (m, 1H); 7.2–7.6 (m, 12H).

Example I-5

(Process C)

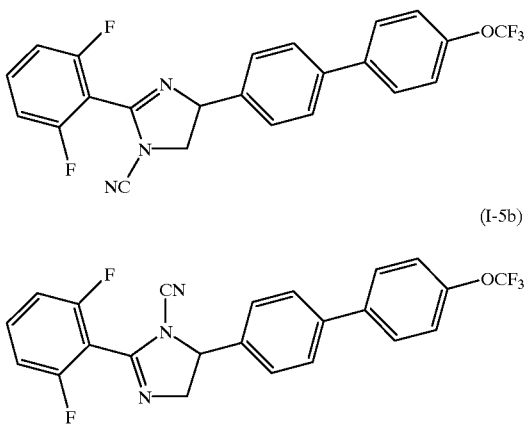

At 5° C., 22.9 g (0.37 mol) of cyanogen chloride were introduced into a solution of 2.6 g (6.1 mmol) of 4-(4'-trifluoromethoxy-4-biphenylyl)-2-(2,6-difluorophenyl)-4,5-dihydro-1H-imidazole (for example from Example V-1) in 260 ml of dichloro-methane. The mixture was stirred at 0–5° C. for 45 minutes. Subsequently, a solution of 15.6 g (0.39 mol) of sodium hydroxide in 140 ml of water (10% strength base) was added dropwise. The organic phase was removed and the aqueous phase was then extracted with dichloromethane, and the combined organic phases were washed with water, dried and concentrated under water-pump vacuum (30° C.). This gave 2.9 g of crude product which were separated by column chromatography (silica gel Ø=3 cm, l=30 cm; gradient cyclohexane: ethyl acetate 7:1→5:1). This gave 1.55 g (57% of theory) of 1-cyano-4-(4'-trifluoromethoxy-4-biphenylyl)-2-(2,6-difluorophenyl)-4,5-dihydro-1H-imidazole (I-5a) and 0.80 g (30% of theory) of 3-cyano-4-(4'-trifluoromethoxy-4-biphenylyl)-2-(2,6-difluorophenyl)-4,5-dihydro-3H-imidazole (I-5b).

(I-5a): m.p.: 123–124° C; (I-5b): $^1$H NMR (500 MHz, DMSO): δ [ppm] 4.1 (m, 1H); 4.7 (m, 1H); 5.7 (m, 1H); 7.4–7.9 (m, 11H).

Example I-6

(Process C)

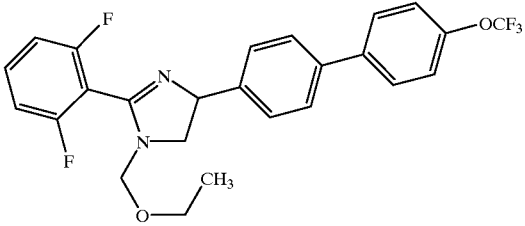

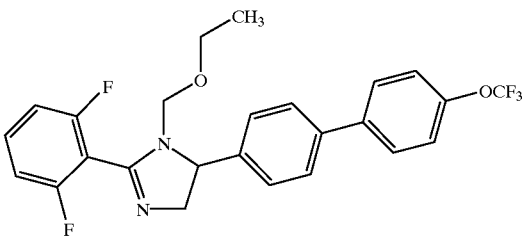

At 0° C., a solution of 1.5 g (3.6 mmol) of 4-(4'-trifluoromethoxy-4-biphenylyl)-2-(2,6-difluorophenyl)-4,5-dihydro-1H-imidazole (for example from Example V-1) in 15 ml of dichloromethane was admixed first with 0.75 ml (0.55 g; 5.4 mmol) of triethylamine and then with 4 ml (0.41 g; 4.32 mmol) of chloromethyl ethyl ether. After the mixture had been stirred overnight, approximately 50% of starting material were still present (TLC). A further 0.25 ml of triethylamine and 0.17 ml of the ether were introduced. Since no further reaction could be detected, another 0.25 ml of triethylamine was added and the mixture was heated to the boil. For work-up, the reaction mixture was extracted with 10% strength citric acid and 1N aqueous sodium hydroxide solution, dried, concentrated and chromatographed over a silica gel column (Ø=3 cm, l=30 cm). Elution with cyclohexane/ethyl acetate using a 5-stage gradient from 20:1 to 3:1 gave, as second fraction, 0.30 g (17% of theory) of 1-ethoxymethyl-4-(4'-trifluoromethoxy-4-biphenylyl)-2-(2,6-difluorophenyl)-4,5-di-hydro-1H-imidazole (I-6a) and, as third fraction, 0.34 g (20% of theory) of 3-ethoxymethyl-4-(4'-trifluoromethoxy-4-biphenylyl)-2-(2,6-difluorophenyl)-4,5-di-hydro-3H-imidazole (I-6b).

(I-6a): $^1$H NMR (400 MHz, DMSO): δ [ppm] 1.0 (t, 3H); 3.2–3.5 (m, 2+1H); 4.1 (m, 1H); 4.4 (s, 1H); 5.3 (m, 1H); 7.2–7.9 (m, 11H);

(I-6b): $^1$H NMR (400 MHz, DMSO): δ [ppm] 0.9 (t, 3H); 3.1–3.3 (m, 2H); 3.7 (m, 1H); 4.2 (m, 2H); 4.4 (m, 1H); 5.1 (m, 1H); 7.2–7.9 (m, 11H);

Example I-7

(Process C)

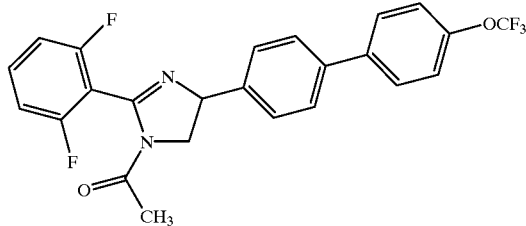
(I-7a)

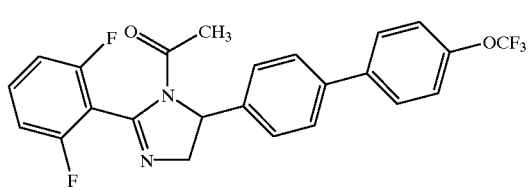
(I-7b)

1.5 g (3.6 mmol) of 4-(4'-trifluoromethoxy-4-biphenylyl)-2-(2,6-difluorophenyl)-4,5-dihydro-1H-imidazole (for example from Example V-1) were dissolved in 20 ml of toluene, admixed with 1.7 ml (1.84 g; 18 mmol) of acetic anhydride and boiled under reflux for 1 h. The mixture was then concentrated and the residue was recrystallized from a mixture of cyclohexane and ethyl acetate. This gave 1.07 g (65% of theory) of 1-acetyl-4-(4'-trifluoromethoxy-4-biphenylyl)-2-(2,6-difluorophenyl)-4,5-dihydro-1H-imidazole (I-7a). 0.6 g of concentration residue from the mother liquor was separated by column chromatography (silica gel; Ø=3cm, 1=30 cm; cyclohexane:ethyl acetate=5:1). 0.12 g (7% of theory) of 3-acetyl4-(4'-trifluoromethoxy-4-biphenylyl)-2-(2,6-difluorophenyl)-4,5-dihydro-3H-imidazole (I-7b) was obtained as second fraction as an oil.

(I-7a): m.p.: 109–111° C; (I-7b): $^1$H-NMR (400 MHz, DMSO): δ [ppm] 1.9 (t, 3H); 3.7 (m, 1H); 4.6 (m, 1H); 5.6 (m, 1H); 7.2–7.9 (m, 11H).

Example I-8

(Process D)

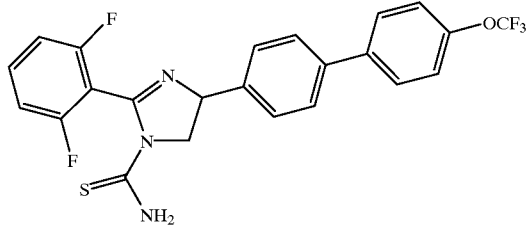

1.0 g (2.3 mmol) of 1-cyano-4-(4'-trifluoromethoxy-4-biphenylyl)-2-(2,6-difluorophenyl)-4,5-dihydro-1H-imidazole (for example from Example I-5, compound I-5a) were initially charged under argon in 15 ml of pyridine p.a. At room temperature, hydrogen sulphide was introduced for 30 min, the mixture was stirred for another 1.5 h and the remaining hydrogen sulphide was subsequently flushed out. For work-up, the mixture was concentrated under reduced pressure, toluene was added and the mixture was reconcentrated. The residue of 1.2 g was purified by chromatography (silica gel; Ø=3 cm, 1=30 cm; gradient cyclohexane:ethyl acetate 4:1→1:2). The resulting crystalline product which melted at 93–95° C. contained, according to 2D-NMR spectrum and GC-MS, in addition to 10% of the desired 4-(4'-trifluoromethoxy4-biphenylyl)-2-(2,6-difluorophenyl)-1-thiocarbamoyl-4,5-dihydro-1H-imidazole, the non- N-substituted imidazoline (V-1).

MS (CI): mnz: 477 (M$^+$).

Example I-9

(Process D)

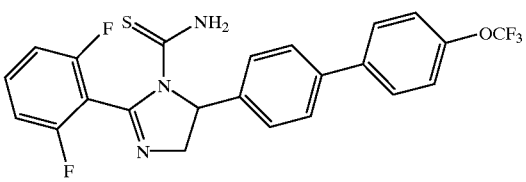

Similarly to Example I-8, 0.5 g (1.15 mmol) of 3-cyano-4-(4'-trifluoromethoxy-4-biphenylyl)-2-(2,6-difluorophenyl)-4,5-dihydro-3H-imidazole (for example from Example I-3, compound I-3b) gave 0.50 g of crude product. Column chromatography (silica gel Ø=3 cm, 1=30 cm; gradient cyclohexane:ethyl acetate 8:1→2:1) gave 0.17 g of N-substituted imidazoline (V-1) which, according to $^1$H NMR spectrum and GC-MS, contained small amounts of the desired 4-(4'-trifluoromethoxy-4-biphenylyl)-2-(2,6-difluorophenyl)-thiocarbamoyl-4,5-dihydro-3H-imidazole.

MS (CI): m/z: 477 (M$^+$).

PREPARATION OF THE PRECURSORS

Example II-1

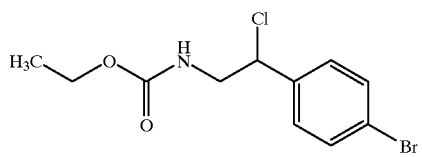

9.8 ml (13.7 g, 0.075 mol) of p-bromostyrene were dissolved in 50 ml of acetonitrile p.a. and a stream of argon was passed over this mixture. At from 5 to 10° C., a solution of 12 g (0.075 mol) of ethyl N,N-dichlorocarbamate in 50 ml of acetonitrile p.a. was added dropwise at such a rate that the temperature did not exceed 10° C. The mixture was subsequently stirred at room temperature for another 3 h. After GC reaction control (about 88% of product), 75 ml of a 20% strength sodium bisulphite solution were added with cooling at from 5 to 10° C. (exothermic reaction). After phase separation, the aqueous phase was extracted with 2×20 ml of diethyl ether. The combined organic phases were extracted with saturated sodium chloride solution and water, dried and concentrated. This gave 22.10 g (96% of theory) of crude ethyl N-[2-(4-bromophenyl)-2-chloroethyl]-carbamate which was directly reacted further.

M.p.: 61–62° C.

Example V-1

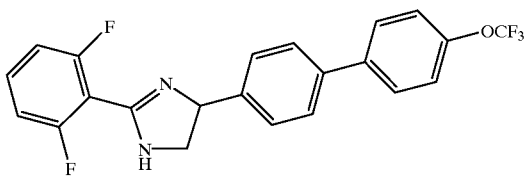

At room temperature, 2 g (4.08 mmol) of 4-(4'-trifluoromethoxy-4-biphenylyl)-1-ethoxycarbonyl-2-(2,6-difluorophenyl)-4,5-dihydro-1H-imidazole (for example from Example II-2) were added to a solution/suspension of 1.1 g (20 mmol) of potassium hydroxide in 15 ml of ethanol p.a. The mixture was stirred under reflux for one hour and the conversion was checked by TLC, and the mixture was then cooled, poured into water and extracted with tert-butyl methyl ether. Drying and concentration of the combined extracts gave 1.7 g of crude product. This was stirred with a mixture of dichloromethane and cyclohexane and the precipitate crystals were filtered off with suction. The mother liquor was concentrated and once more stirred with a small amount of the mixture, giving a second crystal fraction. Yield: 1.00 g (60% of theory) of 4-(4'-trifluoromethoxy-4-biphenylyl)-2-(2,6-difluorophenyl)-4,5-dihydro-1H-imidazole.

M.p.: 125–127° C.

USE EXAMPLES

Example A

Phaedon larvae test

Solvent: 7 parts by weight of dimethylfornamide

Emulsifier: 1 part by weight of alkylaryl polyglycol ether

To produce a suitable preparation of active compound, 1 part by weight of active compound is mixed with the stated amount of solvent and emulsifier, and the concentrate is diluted with water to the desired concentration.

Cabbage leaves (*Brassica oleracea*) are treated by being dipped into the preparation of active compound of the desired concentration and populated with mustard beetle larvae (*Phaedon cochleariae*) while the leaves are still moist.

After the desired period of time, the kill in % is determined. 100% means that all beetle larvae have been killed; 0% means that none of the beetle larvae have been killed.

In this test, an active compound concentration of 0.1%, for example the compounds of Preparation Example I-4, I-5a, I-5b, I-6a, I-6b and I-8 showed a kill of 100% and the compound from Preparation Example I-7a showed a kill of 90%, after 7 days.

Example B

Spodoptera frugiperda test

Solvent: 7 parts by weight of dimethylformamide

Emulsifier: 1 part by weight of alkylaryl polyglycol ether

To prepare a suitable preparation of active compound, 1 part by weight of active compound is mixed with the stated amount of solvent and emulsifier, and the concentrate is diluted with water to the desired concentration.

Cabbage leaves (*Brassica oleracea*) are treated by being dipped into the preparation of active compound of the desired concentration and populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, at an active compound concentration of 0.1%, for example the compounds of Preparation Examples I-4, I-3, I-5a, I-5b, I-6a, I-7a and I-8 showed, after 7 days, a kill of 100%.

Example C

Tetranychus test (OP-resistant/dip treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed, 0% means that none of the spider mites have been killed.

In this test, after 7 days, for example the compounds of Preparation Examples I-3, I-5a, I-5b, I-6a and I-7a showed, at an active compound concentration of 0.01%, a kill of 100%, and the compound of Preparation Example I-8 showed a kill of 95%.

Example D

Blowfly larvae test/development-inhibitory action

Test animals: *Lucilia cuprina* larvae

Solvent: Dimethylsulfoxide 20 mg of active compound are dissolved in 1 ml of dimethyl suiphoxide, and more dilute concentrations are prepared by dilution with dist. water.

Approximately 20 *Lucilia cuprina* larvae are introduced into a test tube which contains approximately 1 cm³ of horse meat and 0.5 ml of the active compound preparation to be tested. After 24 and 48 hours, the efficacy of the preparation of active compound is determined. The test tubes are transferred into a beaker with sand-covered bottom. After a further 2 days, the test tubes are removed and the pupae are counted.

The effect of the preparation of active compound is assessed by the number of the flies which have hatched after 1.5 times the development time of an untreated control. 100% means that none of the flies have hatched; 0% means that all flies have hatched normally.

In this test, the compounds of preparation examples I-3 and I-4a showed, at an active compound concentration of 100 ppm, an efficacy of 100%.

What is claimed is:

1. Compounds of the formula (I)

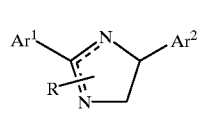

in which

Ar¹ represents the grouping (a)

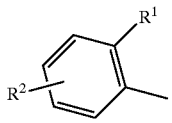
(a)

in which
R² represents halogen, alkyl, alkoxy or halogenoalkoxy and
R² represents hydrogen, halogen, alkyl or alkoxy, Ar² represents the grouping (b) or (c)

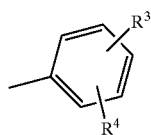
(b)

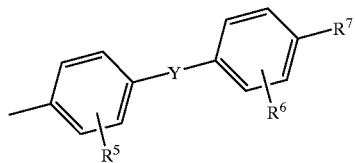
(c)

in which
R³, R⁴, R⁵ and R⁶ independently of one another each represent hydrogen, halogen, alkyl, alkoxy, halogenoalkoxy or halogenoalkylthio,
R⁷ represents hydrogen, halogen, cyano, alkyl, alkoxy, alkylthio, halogenoalkyl, halogenoalkoxy or halogenoalkylthio and
Y represents a direct bond, oxygen, methylene, —O—CH₂— or —CH₂O— and R represents cyano, alkoxyalkyl, formyl, alkylcarbonyl, alkoxycarbonyl or —C(X)—NHR⁸ in which
X represents oxygen or sulphur and
R⁸ represents hydrogen or alkyl.

2. Compounds of the formula (I) according to claim 1 in which
Ar¹ represents the grouping (a)

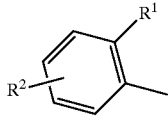

in which
R¹ represents halogen, $C_1$–$C_3$-alkyl, $C_1$–$C_3$-alkoxy or $C_1$–$C_3$-halogenoalkoxy and
R² represents hydrogen, halogen, $C_1$–$C_3$-alkyl or $C_1$–$C_3$-alkoxy, Ar² represents the grouping (b) or (c)

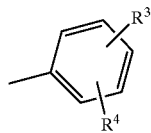
(b)

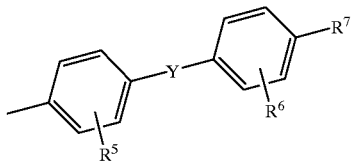
(c)

in which
R³, R⁴, R⁵ and R⁶ independently of one another each represent hydrogen, halogen, $C_1$–$C_{12}$-alkyl or $C_1$–$C_{12}$-alkoxy,
R⁷ represents hydrogen, halogen, cyano, $C_1$–$C_6$-alkyl, $C_1$–$C_6$-alkoxy, $C_1$–$C_6$-alkylthio, $C_1$–$C_6$-halogenoalkyl, $C_1$–$C_4$-halogenoalkoxy or $C_1$–$C_4$-halogenoalkylthio,
Y represents a direct bond or oxygen and R represents cyano, $C_1$–$C_4$-alkoxy-$C_1$–$C_4$-alkyl, $C_1$–$C_4$-alkylcarbonyl, $C_1$–$C_4$-alkoxycarbonyl or —C(X)—NHR⁸ in which
X represents oxygen or sulphur and
R⁸ represents hydrogen or $C_1$–$C_4$-alkyl.

3. Compounds of the formula (I) according to claim 1 in which
Ar¹ represents the grouping (a)

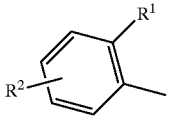

in which
R¹ represents fluorine, chlorine, bromine, iodine, $C_1$–$C_3$-alkyl and $C_1$–$C_3$-alkoxy and
R² represents hydrogen, fluorine, chlorine, bromine, $C_1$–$C_3$-alkyl or $C_1$–$C_3$-alkoxy, Ar² represents the groupings (b-a) or (c-a)

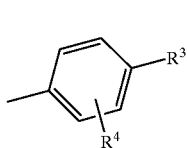
(b-a)

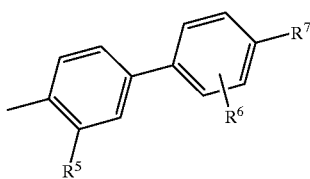
(c-a)

in which
R³, R⁴, R⁵ and R⁶ independently of one another each represent hydrogen, fluorine, chlorine, bromine, iodine, $C_1$–$C_6$-alkyl or $C_1$–$C_6$-alkoxy,
R⁷ represents hydrogen, fluorine, chlorine, bromine, iodine, cyano, $C_1$–$C_4$-alkyl, $C_1$–$C_4$-alkoxy, $C_1$–$C_4$-alkylthio, fluorine- or chlorine-substituted $C_1$–$C_4$-alkyl, $C_1$–$C_4$-alkoxy or $C_1$–$C_4$-alkylthio, R represents cyano, $C_1$–$C_3$-alkoxy-$C_1$–$C_3$-alkyl, $C_1$–$C_3$-alkylcarbonyl, $C_1$–$C_2$-alkoxycarbonyl or —C(X)—NHR⁸ in which
R⁸ represents hydrogen or $C_1$–$C_4$-alkyl,
X represents oxygen or sulphur.

4. Compounds of the formula (I) according to claim 1 in which
Ar¹ represents the grouping (a-1), (a-2) or (a-3)

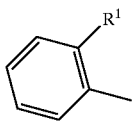 (a-1)

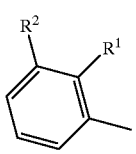 (a-2)

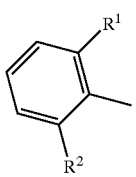 (a-3)

in which
$R^1$ represents fluorine, chlorine, bromine, methyl, ethyl, methoxy or ethoxy and
$R^2$ represents hydrogen, fluorine, chlorine, bromine, methyl, ethyl, methoxy or ethoxy,
Ar² represents the grouping (b-b) or (c-b)

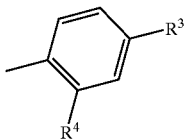 (b-b)

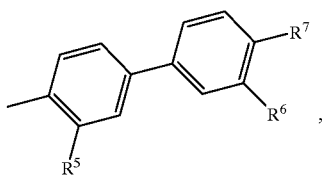 (c-b)

in which
$R^3$, $R^4$, $R^5$ and $R^6$ independently of one another each represent hydrogen, fluorine, chlorine, bromine, methyl, ethyl, n-propyl, isopropyl, n-butyl, isobutyl, sec-butyl, tert-butyl, pentyl, hexyl, methoxy, ethoxy, n-propoxy, isopropoxy, n-butoxy, isobutoxy, sec-butoxy, tert-butoxy, pentyloxy or hexyloxy,
$R^7$ represents fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, methylthio, ethylthio, n-propylthio, isopropylthio, difluoromethyl, trifluoromethyl, dichloromethyl, trichloromethyl, difluoromethoxy, trifluoromethoxy, chlorodifluoromethoxy, 1,1-difluoroethoxy, 1,1,2-trifluoroethoxy, 1,1,2,2-tetrafluoroethoxy, 2-chloro-1,1,2-trifluoroethoxy, 2,2,2-trichloro-1,1-difluoroethoxy, pentafluoroethoxy, difluoromethylthio, trifluoromethylthio, chlorodifluoromethylthio, 1,1-difluoroethylthio, 1,1,2-trifluoroethylthio, 2,2,2-Trifluoroethylthio, 1,1,2,2-tetrafluoroethylthio, 2-chloro-1,1,2-trifluoroethylthio, 2,2,2-trichloro-1,1-difluoroethylthio or pentafluoroethylthio,
R represents cyano, ethoxymethyl, acetyl, propionyl, butyryl, methoxycarbonyl, ethoxycarbonyl or —C(X)NHR⁸ in which
$R^8$ represents hydrogen, methyl or ethyl,
X represents oxygen or sulphur.

5. Process for preparing compounds of the formula (I) according to claim 1, characterized in that
A) diphenylimidazolines of the formula (I-a)

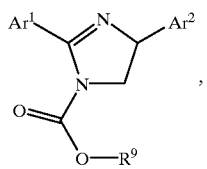 (I-a)

in which
Ar¹ and Ar² are each as defined above and
$R^9$ represents $C_1$–$C_4$-alkyl,
are obtained by condensing β-chlorocarbamates of the formula (II)

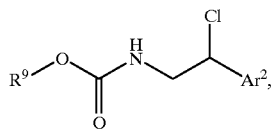 (II)

in which
Ar² and $R^9$ are each as defined above
with benzonitriles of the formula (III)

Ar¹—CN (III), in which
Ar¹ is as defined above
in the presence of sulphuric acid, or
B) diphenylimidazolines of the formula (I-b)

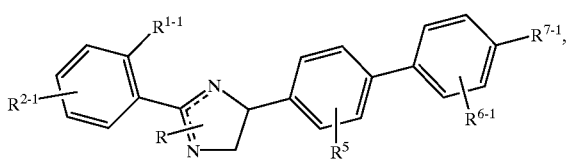 (I-b)

in which
R is as defined above and
$R^{1-1}$ represents fluorine, chlorine, alkyl, alkoxy or halogenoalkoxy,
$R^{2-1}$ represents hydrogen, fluorine, chlorine, alkyl or alkoxy, $R^{5-1}$ and $R^{6-1}$ independently of one another each represent hydrogen, fluorine, chlorine, alkyl, alkoxy, halogenoalkyl or halogenoalkylthio and $R^{7-1}$ represents hydrogen, fluorine, chlorine, cyano, alkyl, alkoxy, alkylthio, halogenoalkyl or halogenoalkylthio are obtained by coupling halogen compounds of the formula (I-c)

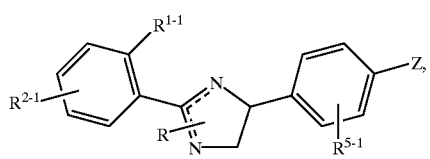
(I-c)

in which

R, $R^{1-1}$, $R^{2-1}$ and $R^{5-1}$ are each as defined above and Z represents bromine or iodine
with boronic acids of the formula (IV)

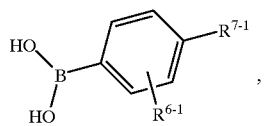
(IV)

in which $R^{6-1}$ and $R^{7-1}$ are each as defined above
in the presence of a catalyst and, if appropriate, in the presence of an acid binder and, if appropriate, in the presence of a diluent, or C) diphenylirnidazolines of the formula (I)

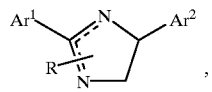
(I)

in which $Ar^1$, $Ar^2$ and R are each as defined above
are obtained by condensing diphenylimnidazolines of the formula (V)

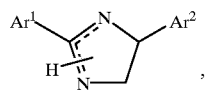
(V)

which are not substituted at nitrogen and in which $Ar^1$ and $Ar^2$ are each as defined above
with compounds of the formula (VI)

R—$X^1$ (VI), in which
R is as defined above and
$X^1$ represents, depending on the radical R, a suitable leaving group
in which
$R^{10}$ represents alkyl or aryl,
if appropriate in the presence of a reaction auxiliary, or D) diphenylirnidazolines of the formula (I-d)

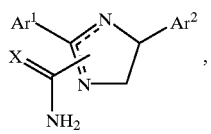
(I-d)

in which
$Ar^1$, $Ar^2$ and X are each as defined above
are obtained by reacting nitrites of the formula (I-e)

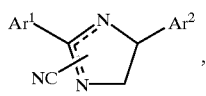
(I-e)

in which
$Ar^1$ and $Ar^2$ are each as defined above
with water or hydrogen sulphide, if appropriate in the presence of a reaction auxiliary.

6. Compounds of the formula (V)

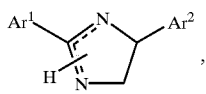
(V)

in which
$Ar^1$ represents the grouping (a)

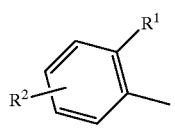
(a)

in which
$R^1$ represents halogen, alkyl, alkoxy or halogenoalkoxy and
$R^2$ represents hydrogen, halogen, alkyl or alkoxy,
$A^2$ represents the grouping (b) or (c)

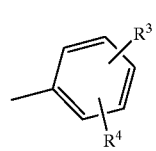
(b)

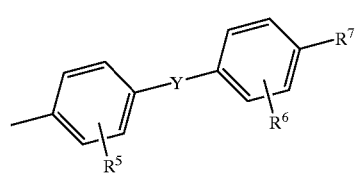
(c)

in which
$R^3$, $R^4$, $R^5$ and $R^6$ independently of one another each represent hydrogen, halogen, alkyl, alkoxy, halogenoalkoxy or halogenoalkylthio,
$R^7$ represents hydrogen, halogen, cyano, alkyl, alkoxy, alkylthio, halogenoalkyl, halogenoalkoxy or halogenoalkylthio and Y represents a direct bond, oxygen, methylene, —O—CH$_2$— or —CH$_2$O—.

7. A pesticide comprising one or more of the compounds of claim 1 and a member selected from the group consisting of liquid solvents, solid carriers, surface-active agents and mixtures thereof.

8. A method for controlling pests selected from the group consisting of insects, arachnids and nematodes comprising allowing an effective amount of one or more compounds of claim 1 to act on said pests and/or their habitat.

9. A process for preparing a pesticide comprising mixing one or more of the compounds of claim 1 with a member selected from the group consisting of liquid solvents, solid carriers, surface-active agents and mixtures thereof.

* * * * *